United States Patent
Lu

(10) Patent No.: US 12,350,178 B2
(45) Date of Patent: Jul. 8, 2025

(54) STENT BRAID PATTERN WITH ENHANCED RADIOPACITY

(71) Applicants: STRYKER CORPORATION, Kalamazoo, MI (US); STRYKER EUROPEAN OPERATIONS LIMITED, Carrigtwohill (IE)

(72) Inventor: Jeffrey Lu, Kalamazoo, MI (US)

(73) Assignees: Stryker Corporation, Kalamazoo, MI (US); Stryker European Operations Limited, Carrigtwohill (IE)

(*) Notice: Subject to any disclaimer, the term of this patent is extended or adjusted under 35 U.S.C. 154(b) by 11 days.

(21) Appl. No.: 18/472,146

(22) Filed: Sep. 21, 2023

(65) Prior Publication Data

US 2024/0009011 A1 Jan. 11, 2024

Related U.S. Application Data

(63) Continuation of application No. 16/538,953, filed on Aug. 13, 2019, now abandoned.

(51) Int. Cl.
| | |
|---|---|
| *A61F 2/90* | (2013.01) |
| *A61L 31/02* | (2006.01) |
| *A61L 31/18* | (2006.01) |

(52) U.S. Cl.
CPC ............... *A61F 2/90* (2013.01); *A61L 31/022* (2013.01); *A61L 31/18* (2013.01); *A61F 2250/0098* (2013.01)

(58) Field of Classification Search
CPC .. A61F 2/90; A61F 2250/0098; A61L 31/022; A61L 31/18; D10B 2509/06; D04C 1/06
See application file for complete search history.

(56) References Cited

U.S. PATENT DOCUMENTS

| | | | |
|---|---|---|---|
| 8,715,314 B1 | 5/2014 | Janardhan et al. | |
| 8,904,914 B2 * | 12/2014 | Janardhan ............... | A61M 1/84 623/1.53 |

(Continued)

FOREIGN PATENT DOCUMENTS

| | | |
|---|---|---|
| EP | 2875798 | 5/2015 |
| EP | 2875833 | 5/2015 |

OTHER PUBLICATIONS

PCT International Search Report and Written Opinion for International Appln. No. PCT/US2020/045079, Applicant Stryker Corporation, dated Oct. 23, 2020 (11 pages).

(Continued)

*Primary Examiner* — Suzette J Gherbi
(74) *Attorney, Agent, or Firm* — Vista IP Law Group, LLP

(57) ABSTRACT

An implantable metallic braid is formed out of groups of filaments of a first material, groups of filaments of a second material different from the first material, and groups of filaments of a third material different from the first material and the second material. The filaments are braided together by a braiding machine and are arranged in a starting filament arrangement on the braiding machine before braiding begins, wherein the first material is a radiopaque material, the second material is a support material, and the third material is a DFT comprising the first and second materials. Different arrangements of the filaments in the starting filament arrangement and in the braid result in different levels of detail that can be observed in images of the braid, wherein certain arrangements of the filaments result in enhanced radiopacity without affecting other mechanical properties of the braid.

16 Claims, 9 Drawing Sheets

(56) References Cited

U.S. PATENT DOCUMENTS

| | | | | |
|---|---|---|---|---|
| 2010/0191319 A1* | 7/2010 | Lilburn | ................... | D04C 3/48 |
| | | | | 87/8 |
| 2015/0148888 A1 | 5/2015 | Milner et al. | | |
| 2017/0354402 A1* | 12/2017 | Lee | ...................... | B21F 45/008 |
| 2019/0239895 A1 | 8/2019 | Dawson et al. | | |

OTHER PUBLICATIONS

Foreign Office Action with Search Report for CN Patent Appln. No. 202080056830X dated Aug. 10, 2024 (with English translation).

\* cited by examiner

STENT BRAID PATTERN WITH ENHANCED RADIOPACITY

RELATED APPLICATION DATA

The present application is a continuation of U.S. patent application Ser. No. 16/538,953, filed Aug. 13, 2019. The foregoing application is hereby incorporated by reference into the present application in its entirety.

FIELD OF THE INVENTION

The present invention is generally directed to body implantable medical devices, and more particularly to stents having enhanced radiopacity as well as favorable mechanical characteristics.

BACKGROUND

Self-expanding medical prostheses, frequently referred to as stents, are well known and commercially available. Devices of these types are used within body vessels for a variety of medical applications. Examples include intravascular stents for treating stenosis, stents for maintaining openings in the urinary, biliary, esophageal and renal tracts, and vena cava filters to capture emboli. Further, stents in blood vessels on which aneurysms are developing are currently well known and widely applied. Particularly fine-meshed stents are usually produced as braided stents, which are used, for example, as flow diverters.

Self-expanding stents are formed from a number of resilient filaments which are helically wound and interwoven in a braided configuration. These stents assume a substantially tubular form in their unloaded or expanded state when they are not subjected to external forces. When subjected to inwardly directed radial forces, these stents are forced into a reduced-radius and extended-length loaded or compressed state. A delivery device which retains the stent in its compressed state is used to deliver the stent to a treatment site through vessels in the body. The flexible nature and reduced radius of the compressed stent enables it to be delivered through relatively small and curved vessels. After the stent is positioned at the treatment site, the delivery device is actuated to release the stent, thereby allowing the stent to self-expand within the body vessel. The delivery device is then detached from the stent and removed from the patient. The stent remains in the vessel at the treatment site.

However, there remains a significant problem during placement of stents and during subsequent examination of patients: because of their small size, these stents are extremely difficult to locate with X-ray. The only parts of the stent that appear on imaging are those with sufficient radiopacity, and the mass and thickness of these radiopaque parts decrease with the diameter of the vessels being treated. Accurate placement of the stent is critical to its effective performance. Accordingly, there is a need to visually perceive the stent as it is being placed within a blood vessel or other body cavity. Further, it is advantageous to visually locate and inspect a previously deployed stent. Typically, enhancing the radiopacity of a stent is accomplished by sacrificing other desired mechanical properties, such as strength, ductility, fatigue failure resistance, size, and the like.

It is an object of the present invention to provide a stent with substantially enhanced radiopacity, without any substantial reduction in the favorable mechanical properties of the stent.

SUMMARY

The present invention is directed to a tubular metallic braid for implantation within a human body. The braid includes a plurality of groups of first filaments of a first material, a plurality of groups of second filaments of a second material different from the first material, and a plurality of groups of third filaments of a third material different from the first material and the second material. The first filaments, second filaments, and third filaments are braided together by a braiding machine, and are arranged in a starting filament arrangement on the braiding machine before braiding begins. In the starting filament arrangement, the first filaments, second filaments and third filaments are positioned such that each group of second filaments is positioned directly adjacent to one of the groups of first filaments, each group of third filaments is positioned directly adjacent to one of the groups of second filaments, both sides of each group of first filaments has one of the groups of second filaments directly adjacent thereto, and each group of second filaments is directly adjacent to one of the groups of first filaments on one side and is directly adjacent to one of the groups of third filaments on the other side.

The second material may be a monofilament or a drawn filled tube (DFT) wire comprising a core and a sheath around the core. The third material may be the other one of the monofilament and the DFT wire. In one embodiment, the second material is the monofilament and the third material is the DFT wire. The first material may be a radiopaque material. The monofilament may be a support material having a tensile strength greater than that of the radiopaque material. The DFT wire may include a radiopaque material and a support material having a tensile strength greater than that of the radiopaque material. The DFT wire core may be made from the radiopaque material, and the DFT wire sheath may be made from the support material. The radiopaque material may be platinum and the support material may be a cobalt chromium alloy. The cobalt chromium alloy may be one of 1058 CoCr alloy and 35N LT® Superalloy. Each group of first filaments may include two filaments of the first material, each group of second filaments may include two filaments of the second material, and each group of third filaments may include two filaments of the third material. Every filament that forms the braid is made of one of the first material, the second material, and the third material. In one exemplary embodiment, the first material is platinum, the second material is a monofilament of a cobalt chromium alloy, and the third material is a DFT wire comprising a platinum core and a sheath made of the cobalt chromium alloy.

Another embodiment of the present invention is directed to a tubular metallic braid for implantation within a human body. The braid includes a plurality of groups of first filaments of a first material, and a plurality of groups of second filaments of a second material different from the first material. One of the first material and the second material is a drawn filled tube (DFT) wire. The first filaments and second filaments are braided together by a braiding machine and are arranged in a starting filament arrangement on the braiding machine before braiding begins. In the starting filament arrangement, each group of second filaments is positioned directly adjacent to one of the groups of first filaments. The first material may be a radiopaque material, and the second material may be the DFT wire. The DFT wire may include a core and a sheath surrounding the core. One of the sheath and the core may be made of a radiopaque material, and the other of the sheath and the core may be made of a support material having a higher tensile strength than the radiopaque material. The DFT wire may include a platinum core and a sheath surrounding the platinum core, the sheath comprising a cobalt chromium alloy. The cobalt chromium alloy may be alloy L605. The platinum core may have a cross-sectional area that is 20% to 30% of a total cross-sectional area of the DFT wire. In one embodiment, every filament that forms the braid is made of either the first material or the second material.

Other and further aspects and features of the disclosed embodiments will become apparent from the ensuing detailed description in view of the accompanying drawings.

BRIEF DESCRIPTION OF THE DRAWINGS

The foregoing and other aspects of embodiments are described in further detail with reference to the accompanying drawings, wherein like reference numerals refer to like elements and the description for like elements shall be applicable for all described embodiments wherever relevant, and in which.

DETAILED DESCRIPTION

The present invention relates generally to implantable, radially expandable stents having unique braid patterns that enhance the radiopacity of the stent without negatively impacting the mechanical properties of the stent. The stent may be a flow-diverting stent used in treating aneurysms or may be used in other endoluminal applications such as in treating stenosis, maintaining openings, or the like. The unique braid pattern provides enhanced radiopacity while maintaining, or improving, the mechanical properties of the tubular stent, compared to existing stents formed of the same or similar materials. As such, the unique radiopaque patterns of the disclosed device provide additional information to physicians, since physicians can more easily determine length, compaction, diameter reduction, and the like.

Braided stents of the same material, size, quantity of filaments, and size of filaments will create different patterns under X-ray depending on the wire pattern placement on a braider machine. Certain braid patterns result in superior edge definition while maintaining a highly visible cross-hatching pattern. It has been found that unique placement of platinum and drawn filled tube (DFT) radiopaque wires in a braid configuration will create distinct segmented patterns under angiography. A specific alternating pattern of platinum wire, DFT wire, and support wire creates a hybrid braid of enhanced radiopacity without compromising radial pressure or stent performance characteristics, such as opening and apposition.

The stents shown in FIGS. 1A-7 are all made of the same quantity, size, and type of filaments, but have different arrangements of the filaments. The stents are substantially tubular bodies formed by braiding filaments, according to any technique known in the art of braiding tubular bodies. As seen in FIGS. 1A, 2A, 3A, and 4A, the arrangement of the wires in the braid has a substantial effect on the level of detail that can be seen in the imaging, both in the smaller diameter stent (shown in the top portion of FIGS. 1A, 2A, 3A, and 4A) and the larger diameter stent (shown in the bottom portion of FIGS. 1A, 2A, 3A, and 4A). FIGS. 1B, 2B, 3B, 4B, and 5-7 each depict a cross-sectional view of an arrangement of filaments, as viewed from the front of a braider, before braiding begins. The properties of the resulting tubular metallic braid are highly dependent on the starting filament arrangements shown in FIGS. 1B, 2B, 3B, 4B, and 5-7.

Figures 1A, 1B:
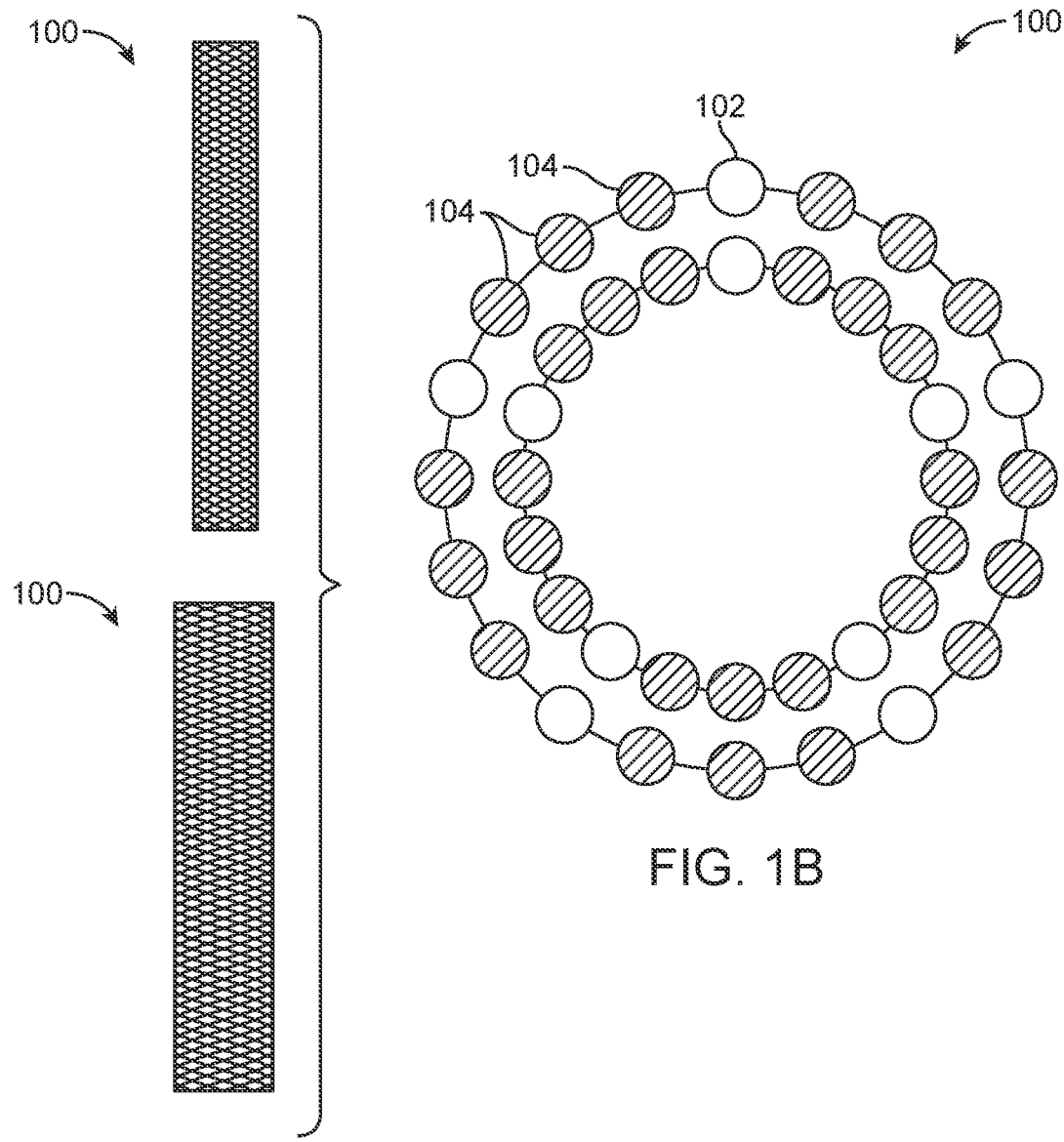
FIGS. 1A, 2A, 3A, and 4A are images of two sizes of tubular metallic braids formed in accordance with different arrangements of filaments in the braids is.
FIGS. 1B, 2B, 3B, and 4B are cross-sectional views of arrangements of filaments taken from the front of a braiding machine before the braiding begins to form the tubular metallic braids shown in FIGS. 1A, 2A, 3A, and 4A, respectively.

The stent shown in FIGS. 1A and 1B is a conventional stent 100 formed of a plurality of filaments braided together. The plurality of filaments includes a first material 102 and a second material 104. As shown in the cross-sectional view of FIG. 1B, in the starting filament arrangement, the filaments of the second material 104 are directly adjacent to the filaments of the first material 102 on both sides of the filaments of the first material 102. Cross-hatching and edge patterns do not show up in the imaging, as shown in FIG. 1A. The edges of the stent 100 shown in FIG. 1A appear as solid lines. In contrast, cross-hatching and edge patterns are more visible in the stent images shown in FIGS. 2A, 3A, and 4A. In particular, with reference to FIG. 4A, the edges of the stent appear as alternating areas of light and dark, rather than a solid line.

The stents in FIGS. 2A-4B are formed of the same materials as the stent 100 shown in FIGS. 1A and 1B. That is, the stents in FIGS. 2A-4B include filaments of the first material 102 and filaments of the second material 104, both of which are the same as the first and second materials 102, 104 used in the stent 100 in FIGS. 1A and 1B. However, the stents in FIGS. 2A-4B further include filaments formed of a third material 106, which is a combination of the first material 102 and the second material 104. The third material 106 is drawn filled tube (DFT) wires that have a core made of the first material 102 or the second material 104, covered with a sheath made of the other of the first material 102 and the second material 104.

In one exemplary embodiment, the first material 102 is a radiopaque material, the second material 104 is a monofilament made of a support material that has a higher tensile strength than the radiopaque material, and the third material 106 is a DFT wire having a core made of a radiopaque material and a sheath made of a support material. Alternatively, the DFT wire may have a core made of the support material and a sheath made of the radiopaque material. The radiopaque material may be platinum, gold, palladium, tungsten, or the like, or an alloy made of two or more of these materials. The support material has a higher tensile strength than the radiopaque material and may be a cobalt chromium (CoCr) alloy, or the like. Other materials that can be used for a support material include (without limitation) L605, Molybdenum, Titanium, or any relatively high-tensile strength alloy of radiopaque material like platinum. The radiopaque and support materials of the DFT wire may the same as those of the first material and the second material, or may be different radiopaque and support materials. One of ordinary skill in the art would readily understand that the braid filaments can be made of any suitable material which is biocompatible and can be worked into a braid.

Figures 2A, 2B:
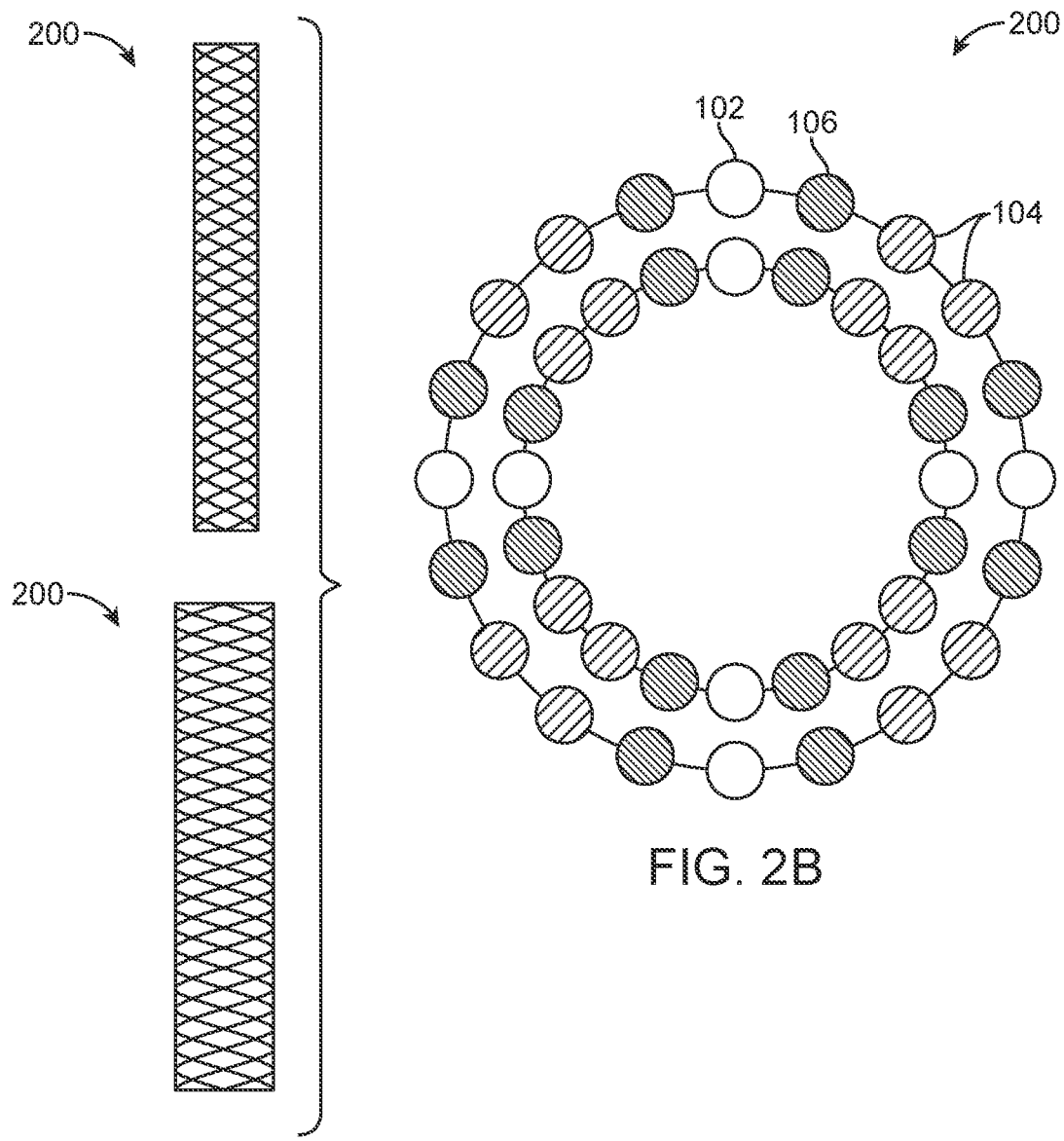

The stent 200 shown in FIG. 2A has a starting filament arrangement as shown in FIG. 2B. Before braiding begins, the filaments are arranged on the braider such that a single filament of the third material 106 is on either side of a single filament of the first material 102. Directly adjacent to the other side of the filament of the third material 106 is a filament of the second material 104. The pattern of: second material 104, third material 106, first material 102, third material 106, and second material 104 is repeated around the stent 200. This is called the "hybrid 8×" configuration. As shown in FIG. 2A, the hybrid 8× braid pattern provides better visibility of the details of the braid, as compared to the stent shown in FIG. 1A. That is, a cross-hatching pattern is more visible in the stent 200 with the hybrid 8× braid pattern than with the conventional stent 100 shown in FIG. 1A.

Figures 3A, 3B:
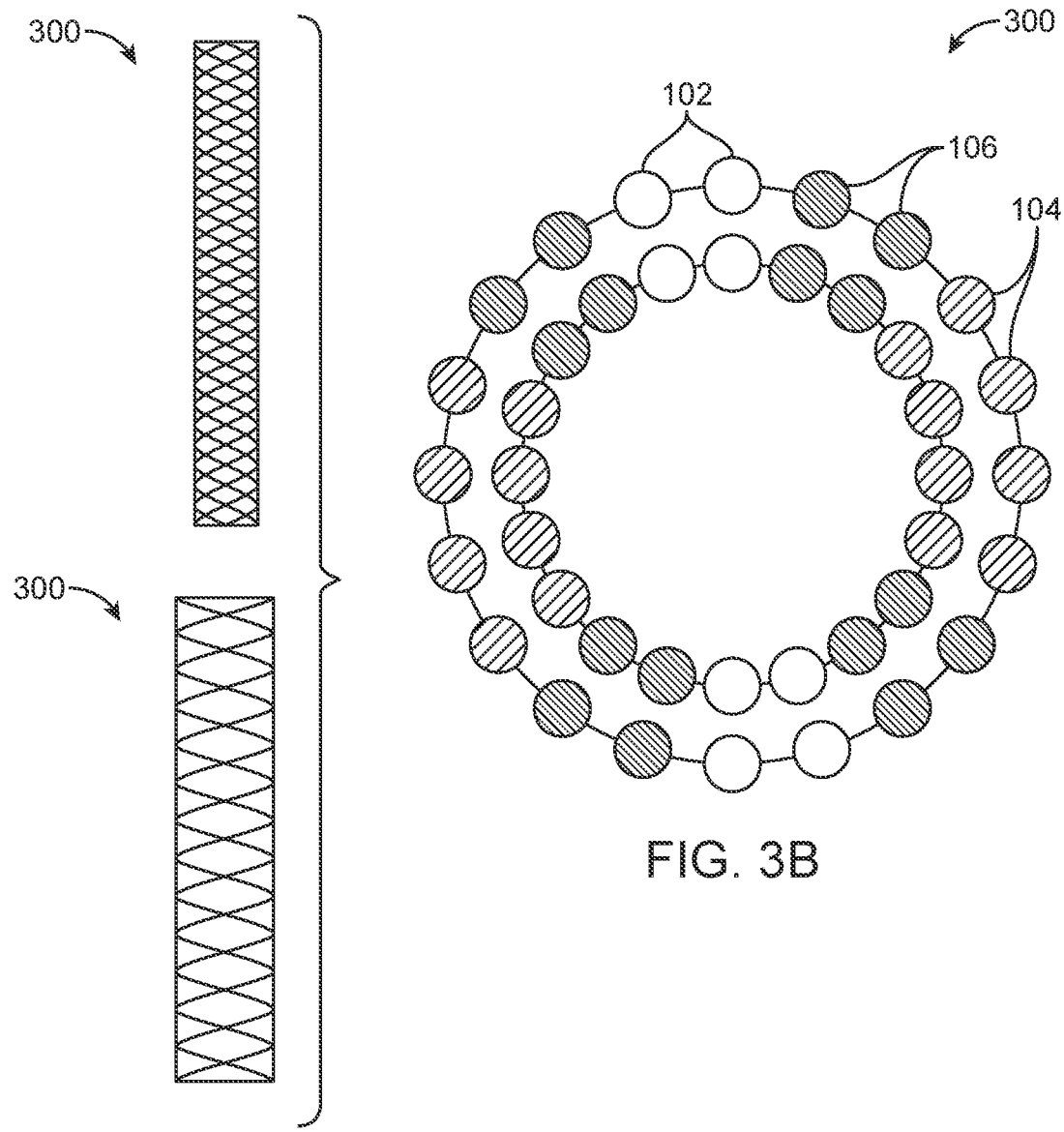

In another embodiment, a stent 300 includes filaments braided together where the filaments are arranged in the pattern shown in FIG. 3B before braiding begins. The starting filament arrangement has a group of filaments of the first material 102 and a group of filaments of the third material 106 positioned directly adjacent to each side of the group of filaments of the first material 102. On the other side of the group of filaments of the third material 106 is a group of filaments of the second material 104. In this example, there are two filaments in each group of filaments. However, it should be readily understood that each group may include three or more filaments. The pattern of: two filaments of the second material 104, two filaments of the third material 106, two filaments of the first material 102, two filaments of the third material 106, and two filaments of the second material 104 is repeated around the stent 300. This pattern is called the "hybrid double 4×" configuration. As shown in FIG. 3A, the hybrid double 4× pattern results in better visibility of the cross-hatch pattern and slightly better edge definition, as compared to the stents in FIGS. 1A and 2A.

Figures 4A, 4B:
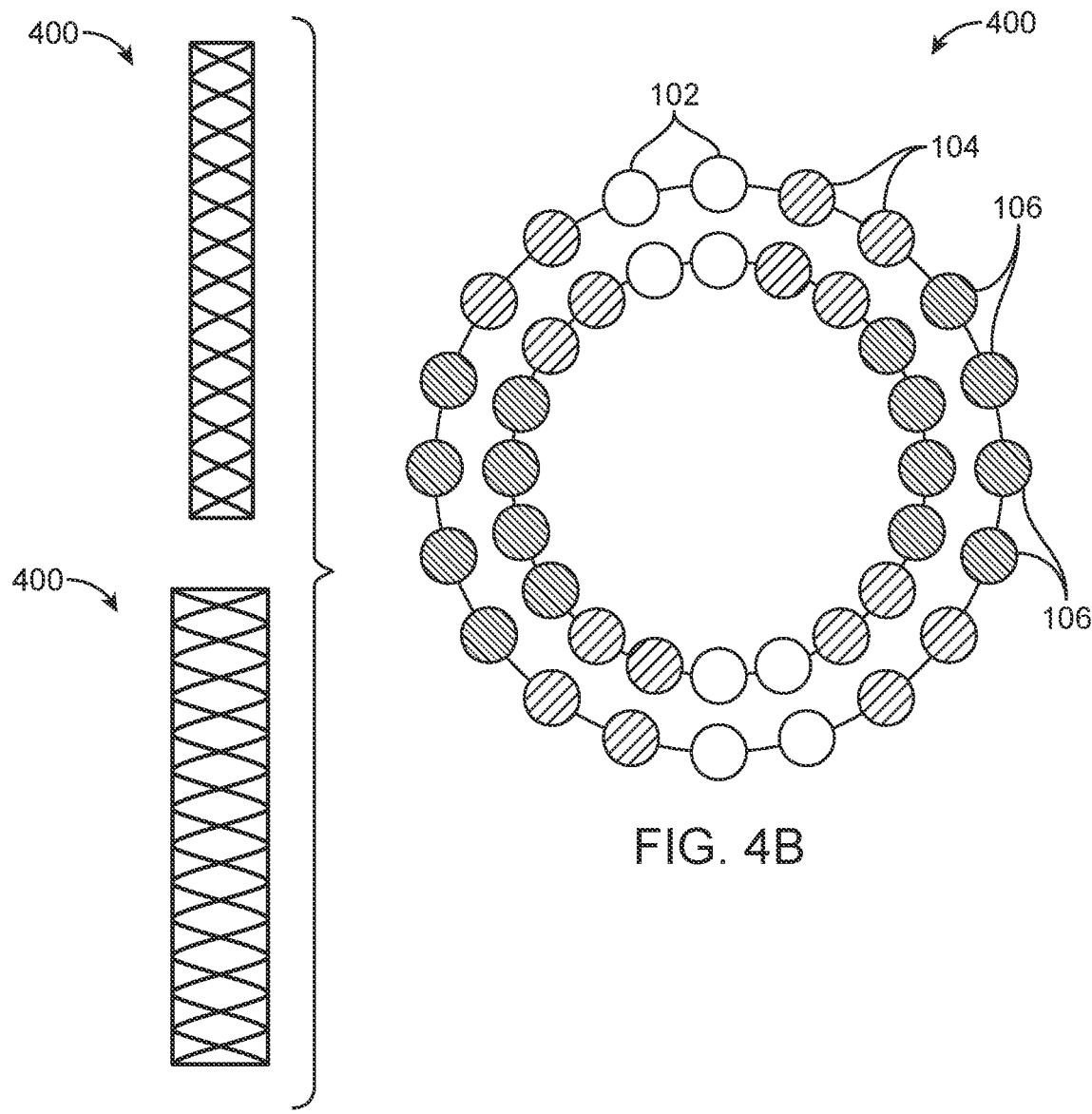

In yet another embodiment, a stent 400 includes filaments braided together where the filaments are arranged in the pattern shown in FIG. 4B before braiding begins. The starting filament arrangement is similar to that shown in FIG. 3B, except that the third material 106 and second material 104 are switched. That is, both sides of a group of filaments of the first material 102 are placed directly adjacent to a group of filaments of the second material 104. A group of filaments of the third material 106 is placed directly adjacent to the other side of the group of filaments of the second material 104. In this example, there are two filaments in each group of filaments. The pattern of: two filaments of the third material 106, two filaments of the second material 104, two filaments of the first material 102, two filaments of the second material 104, and two filaments of the third material 106 is repeated around the stent 400. This pattern is called the "hybrid double 8×" configuration. As shown in FIG. 4A, compared to the other embodiments, the hybrid double 8× pattern results in better visibility of the cross-hatch pattern of the filaments and also results in better edge definition along the sides of the stent 400. That is, the edge of the stent 400 appears as alternating areas of light and dark rather than a solid line.

Figure 5:
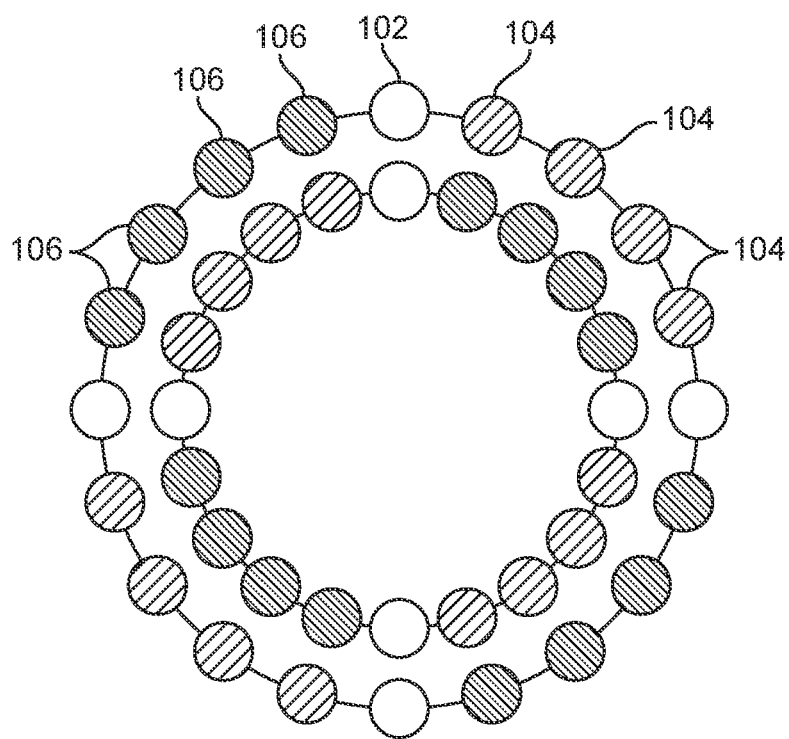
FIGS. 5-7 are cross-sectional views of alternative embodiments of arrangements of filaments taken from the front of a braiding machine before the braiding begins.

Another example of a starting filament arrangement is depicted in FIG. 5. In this example, two filaments of a second material 104 are directly adjacent to one side of a single filament of the first material 102, and two filaments of the third material 106 are directly adjacent to the other side of the single filament of the first material 102. This pattern of: four filaments of the second material 104, a single filament of the first material 102, four filaments of the third material 106, and a single filament of the first material 102 is repeated around the stent. This pattern is called the "hybrid 4×" configuration. While the hybrid 4× braid pattern may result in a stent with enhanced radiopacity, it was found that the braid opening and apposition was abrupt compared to other braid configurations.

Figure 6:
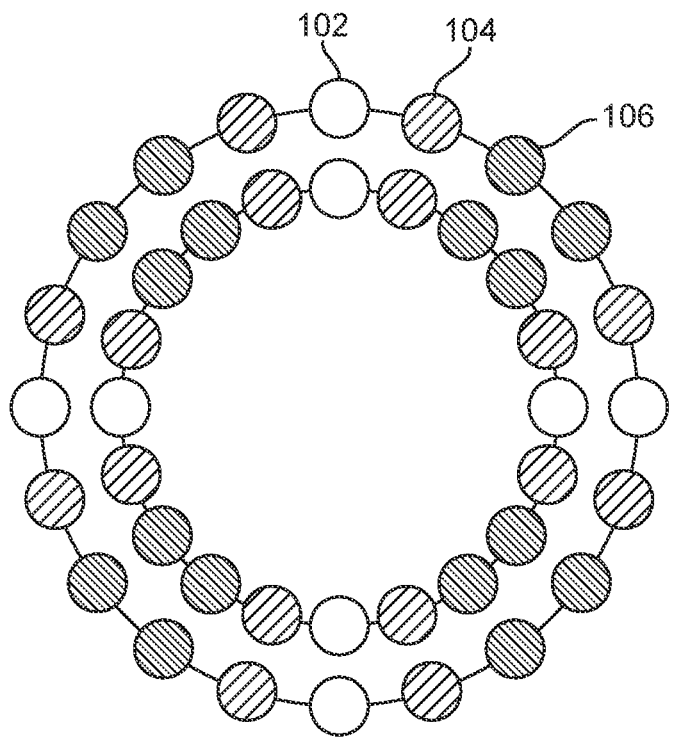

In yet another example of a starting filament arrangement for a stent, shown in FIG. 6, a single filament of the first material 102 is surrounded on both sides by a single filament of the second material 104. The other side of the single filament of the second material 104 is directly adjacent to a single filament of the third material 106. This pattern of: single filament of third material 106, single filament of second material 104, single filament of first material 102, single filament of second material 104, and single filament of third material 106 is repeated around the stent. This pattern is called the "hybrid 16×" configuration.

Figure 7:
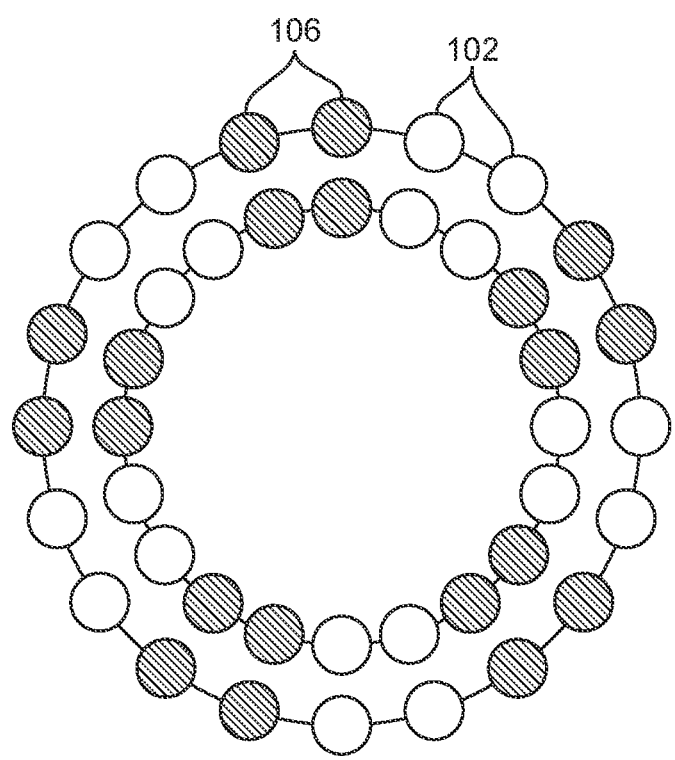

It is notable that all the stents shown in FIGS. 1A-6 are made of the same materials and have the same number of filaments. In one example, the materials of the stents are platinum and cobalt chromium alloys. The examples shown in FIGS. 2A-6 further include DFT wires formed of platinum and cobalt chromium alloys. Every filament that forms the stents in FIGS. 2A-6 is made of the first material, the second material, or the third material. Each of the embodiments shown in FIGS. 1A-6 include 40 filaments, but one of ordinary skill in the art would readily understand that any number of filaments could be used. Further, one of ordinary skill in the art would understand that other materials besides platinum and cobalt chromium alloys could be used for the filaments of the braided stent. Examples of cobalt chromium alloys that may be used in making the stents include 1058 CoCr alloy, alloy L605, 35N LT® Superalloy, and the like. Depending on the ultimate tensile strength of the third material 106 (the DFT wire), the second material 104 (the monofilament) may not be necessary. For example, it was found that when the DFT wire was formed of a platinum core having a cross-sectional area that is 20% to 30% of the total cross-sectional area of the DFT wire, and an outer sheath of alloy L605, the monofilament is not necessary. Alloy L605 has a high ultimate tensile strength relative to other alloys, such as 1058 CoCr alloy. An example of a stent that includes only the first material 102 and the third material 106 is depicted in FIG. 7. Every filament that forms the stent in FIG. 7 is made of the first material 102 or the third material 106. In another embodiment, it was found that when the tubular braid included DFT wire formed of a platinum core having a cross-sectional area that is 28% of the total cross-section of the DFT wire, and an outer sheath of 1058 CoCr alloy, the second material 104 monofilament is necessary in order to enhance the strength of the stent and achieve sufficient radial pressure.

Figure 8:
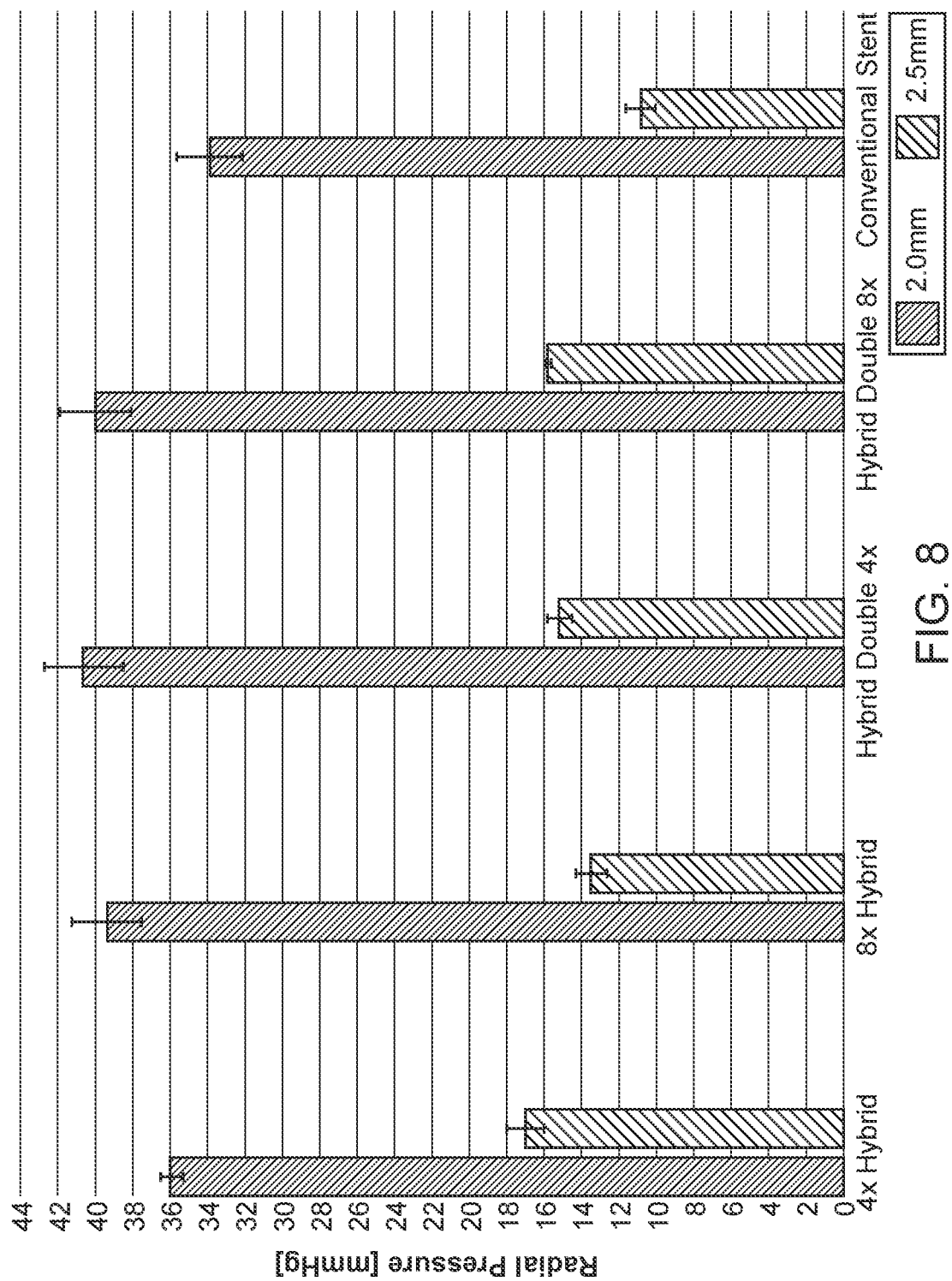
FIGS. 8 and 9 are charts depicting a comparison of the radial pressure performance of the tubular metallic braids of the exemplary embodiments.
Figure 9:
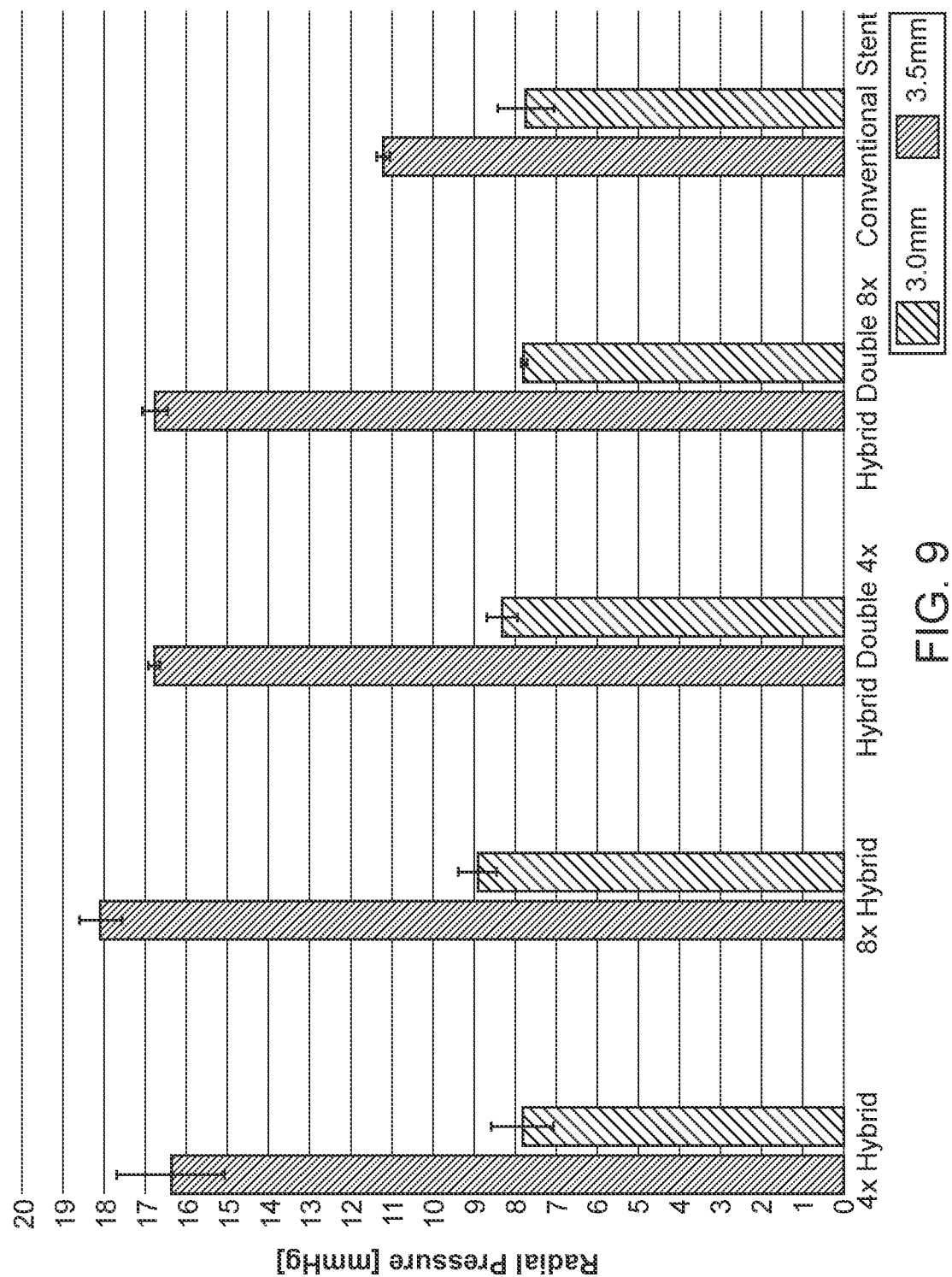

As discussed above, the pattern of the filaments used in the braid of the stent affects the radiopacity of the stent. Some of the braid patterns (e.g., the pattern shown in FIG. 4B) provide higher definition images of the details of the stent. However, the braid pattern has been shown to have negligible effect on the mechanical properties of the stent. As shown in FIGS. 8 and 9, the braid pattern does not have much, if any, effect on the radial pressure performance of the stent. FIG. 8 depicts the radial pressures of the 2 mm and 2.5 mm compressed diameter stents having the braid patterns in accordance with the embodiments discussed above. As shown in FIG. 8, the radial pressures of these stents are comparable to that of the conventional stent, which is depicted on the right side of the graph.

Similarly, FIG. 9 depicts the radial pressures of the 3 mm and 3.5 mm compressed diameter stents having the braid patterns in accordance with the embodiments described herein. As shown in FIG. 9, the radial pressures of these stents are comparable to that of the conventional stent, which is depicted on the right side of the graph.

Figure 10A:
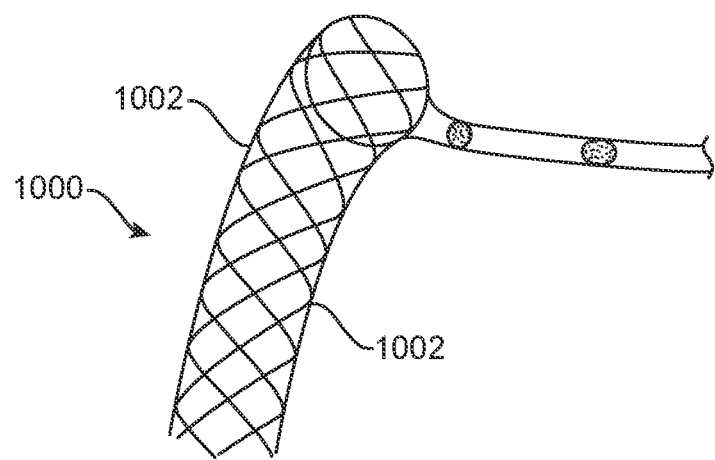
FIGS. 10A and 10B are images of a conventional stent and a stent in accordance with the embodiments herein, respectively, being deployed in a body lumen.
Figure 10B:
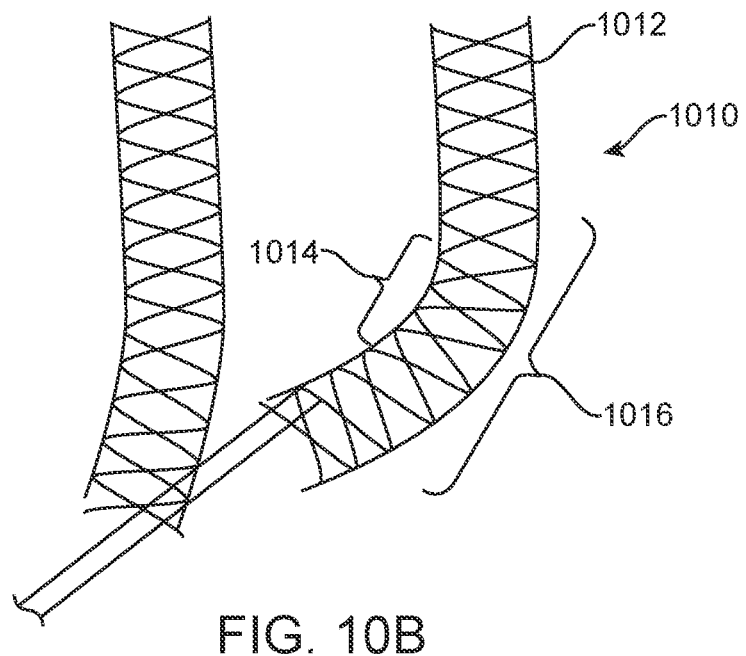

FIG. 10A is an image of a conventional stent 1000, such as the stent shown in FIGS. 1A and 1B. The edges 1002 of the stent 1000 appear as a solid line, making it difficult for the physician to see the filaments, and to visualize whether the stent is expanded or compressed. In contrast, FIG. 10B depicts deployment of a stent 1010 that has a braid pattern in accordance with the embodiments described herein. The edges 1012 of the stent in FIG. 10B appear as alternating dark areas and light areas. As such, the physician is able to see which areas of the stent 1010 are compressed, and which areas are expanded. The compressed areas 1014 appear as darker, shorter segments, while the expanded areas 1016 appear as lighter, longer segments. This visibility is important in, for example, aneurysm treatment in which a forward force may be used to compact the stent lengthwise in the area of the neck of the aneurysm. With the enhanced radiopacity of the braid patterns disclosed herein, the physician can see that the stent is compacted in order to effectively divert blood flow away from the aneurysm. The enhanced radiopacity further allows the physician to see if the device is deployed properly either in terms of position or radial orientation with respect to the entrance to the aneurysm.

While particular embodiments illustrating variations of the many aspects of the disclosed inventions have been disclosed and described herein, such disclosure is provided for purposes of explanation and illustration only. Thus, various changes and modifications may be made to the disclosed embodiments without departing from the scope of the claims. For example, not all of the components described in the embodiments may be necessary for any particular embodiment, and the disclosed inventions may include any suitable combination of the described components. Accordingly, the disclosed inventions should not be limited, except as set forth in the following claims, and their equivalents.

What is claimed is:

1. A method of manufacturing an implantable braid comprising a plurality of groups of first filaments, second filaments, and third filaments, each of the first filaments being formed out of a radiopaque material, each of the second filaments being a monofilament formed out of a support material having a tensile strength greater than a tensile strength of the radiopaque material, and each of the third filaments being a drawn filled tube (DFT) wire comprising a core formed out of one of a radiopaque material and a support material, and a sheath around the core formed of the other of the radiopaque material and the support material, wherein the support material of the DFT wire has a tensile strength greater than a tensile strength of the radiopaque material of the DFT wire, the method comprising:

arranging the groups of first filaments, second filaments, and third filaments in a starting filament arrangement on a braiding machine in which at least one group of first filaments is not directly adjacent to any one of the groups of third filaments; and braiding the starting arrangement of first filaments, second filaments, and third filaments together to form the implantable braid.

2. The method of claim 1, wherein the core of the DFT wire is formed out of the radiopaque material, and the outer sheath of the DFT wire is formed out of the support material.

3. The method of claim 1, wherein the core of the DFT wire is formed out of the support material, and the outer sheath of the DFT wire is formed out of the radiopaque material.

4. The method of claim 1, wherein the radiopaque material and support material of the third filaments are respectively the same as the radiopaque material of the first filaments and the support material of the second filaments.

5. The method of claim 4, wherein the radiopaque material of the first filaments or the radiopaque material of the third filaments is platinum and the support material of the first filaments or the support material of the third filaments is cobalt chromium alloy.

6. The method of claim 5, wherein the cobalt chromium alloy is one of 1058 CoCr alloy and 35N LT® Superalloy.

7. The method of claim 1, wherein the radiopaque material of the first filaments or the radiopaque material of the third filaments is one platinum, gold, palladium, tungsten, or an alloy of two or more of these materials, and the support material of the second filaments or the support material of the third filaments is one of cobalt chromium (CoCr) alloy, molybdenum, and titanium.

8. The method of claim 1, wherein the radiopaque material of the first filaments is platinum, the support material of the second filaments is cobalt chromium alloy, and the DFT wire comprises a platinum core and a sheath made of the cobalt chromium alloy.

9. The method of claim 1, wherein the braid is tubular.

10. The method of claim 1, wherein the DFT wire comprises a platinum core and a cobalt chromium alloy sheath surrounding the platinum core.

11. The method of claim 10, wherein the cobalt chromium alloy is alloy L605.

12. The method of claim 10, wherein the platinum core has a cross-sectional area between 20% to 30% of a total cross-sectional area of the DFT wire.

13. The method of claim 1, wherein every filament of the group of first filaments that forms the braid is made of the radiopaque material, and every filament of the group of second filaments that forms the braid is made of the support material.

14. The method of claim 1, wherein none of the groups of first filaments is directly adjacent to any one of the groups of third filaments.

15. The method of claim 14, wherein each group of first filaments is positioned directly between two groups of the second filaments, and each group of third elements is positioned directly between two groups of second filaments.

16. The method of claim 15, wherein the starting filament arrangement is a hybrid double 8x configuration.

* * * * *